United States Patent
Gruca, Jr. et al.

(10) Patent No.: US 9,038,473 B2
(45) Date of Patent: May 26, 2015

(54) ENERGY ABSORBENT ULTRASONIC INSPECTION SYSTEM WITH LASER POINTER

(75) Inventors: Karl M. Gruca, Jr., Palm Beach Gardens, FL (US); Jeffrey A. Umbach, Palm Beach Gardens, FL (US)

(73) Assignee: United Technologies Corporation, Hartford, CT (US)

( * ) Notice: Subject to any disclaimer, the term of this patent is extended or adjusted under 35 U.S.C. 154(b) by 693 days.

(21) Appl. No.: 13/335,425

(22) Filed: Dec. 22, 2011

(65) Prior Publication Data

US 2013/0160553 A1   Jun. 27, 2013

(51) Int. Cl.
G01N 29/265 (2006.01)
G01N 29/04 (2006.01)

(52) U.S. Cl.
CPC ...... *G01N 29/048* (2013.01); *G01N 2291/0289* (2013.01)

(58) Field of Classification Search
CPC .. G01N 29/223; G01N 29/225; G01N 29/265
USPC .............................. 73/633, 634, 865.5, 865.8
See application file for complete search history.

(56) References Cited

U.S. PATENT DOCUMENTS

| | | | |
|---|---|---|---|
| 4,981,353 A | 1/1991 | Murakawa et al. | |
| 5,107,709 A * | 4/1992 | McCarty | 73/655 |
| 5,773,721 A * | 6/1998 | Bashyam | 73/596 |
| 5,809,099 A | 9/1998 | Kim et al. | |
| 6,157,591 A * | 12/2000 | Krantz | 367/99 |
| 7,076,335 B2 | 7/2006 | Seemann | |
| 7,237,438 B1 | 7/2007 | Umbach et al. | |
| 7,697,727 B2 | 4/2010 | Xu et al. | |
| 7,721,607 B2 | 5/2010 | Kurkcu et al. | |
| 7,775,111 B2 | 8/2010 | Bentzel | |
| 8,616,062 B2 * | 12/2013 | Kono et al. | 73/643 |
| 2004/0154402 A1 | 8/2004 | Drake, Jr. | |
| 2009/0126494 A1 | 5/2009 | Karasawa et al. | |
| 2010/0278008 A1 * | 11/2010 | Ammar | 367/7 |
| 2011/0023585 A1 * | 2/2011 | Izikoff | 73/40.5 A |
| 2011/0030478 A1 * | 2/2011 | Park et al. | 73/622 |
| 2013/0145850 A1 * | 6/2013 | Lute et al. | 73/619 |

FOREIGN PATENT DOCUMENTS

| | | |
|---|---|---|
| EP | 0278791 | 8/1988 |
| SU | 428271 | 5/1974 |
| WO | 8700670 | 1/1987 |
| WO | 2009083674 | 7/2009 |

* cited by examiner

*Primary Examiner* — Laura Martin
*Assistant Examiner* — Rose M Miller
(74) *Attorney, Agent, or Firm* — O'Shea Getz P.C.

(57) ABSTRACT

A system is provided for inspecting a workpiece that includes a workpiece defect and a workpiece surface. The system includes a laser pointer connected to an ultrasonic inspection system. The ultrasonic inspection system includes an ultrasonic transducer that directs sound waves to the workpiece defect, where the sound waves contact the workpiece surface at a workpiece surface location. The laser pointer directs a laser beam against the workpiece surface to visually annunciate the workpiece surface location.

10 Claims, 4 Drawing Sheets

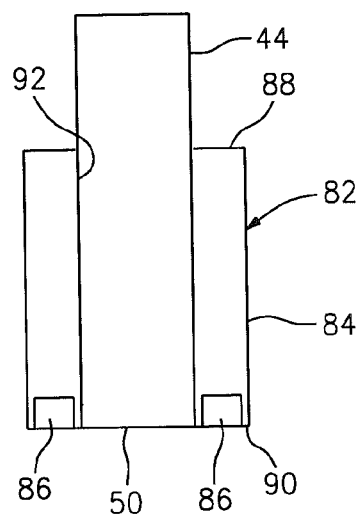
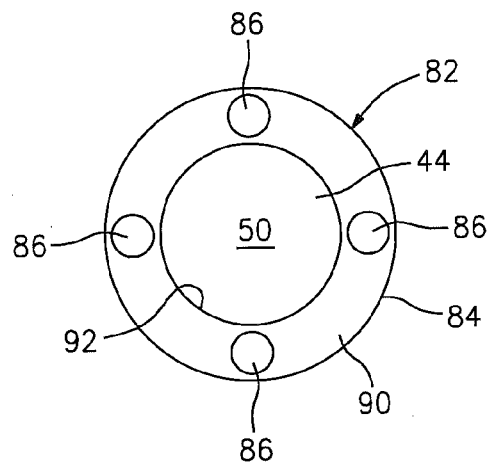
*FIG. 6*  *FIG. 7*
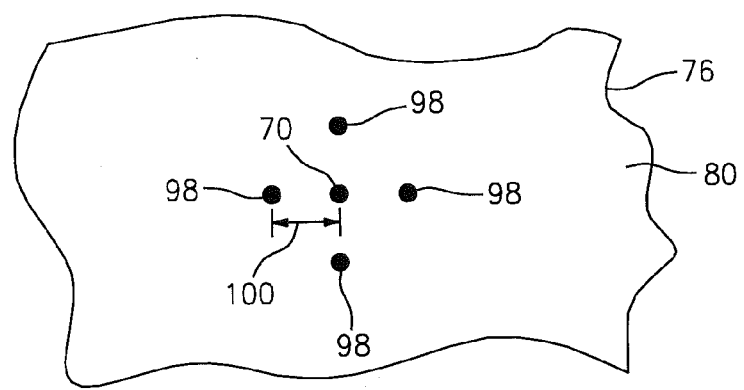
*FIG. 8*

ENERGY ABSORBENT ULTRASONIC INSPECTION SYSTEM WITH LASER POINTER

BACKGROUND OF THE INVENTION

1. Technical Field

The present invention relates to ultrasonic inspection and, in particular, to a system for visually marking a workpiece defect detected during an ultrasonic inspection.

2. Background Information

A typical ultrasonic, non-contact inspection system includes an ultrasonic transducer arranged within an acoustic couplant (e.g., water) next to a workpiece (e.g., a component of a gas turbine engine). During operation, the ultrasonic transducer may direct ultrasonic sound waves through the acoustic couplant and into the workpiece. Portions of the sound waves may reflect back towards the ultrasonic transducer when the sound waves contact various obstructions such as, for example, the workpiece surface and/or internal workpiece defects (e.g., voids in the workpiece material). The ultrasonic transducer may receive the reflected sound waves, and the inspection system may process the sound waves to determine whether the workpiece includes an internal workpiece defect. Determining the location of the workpiece defect within the workpiece, however, may be difficult since sound waves are invisible to the naked eye.

There is a need for an ultrasonic inspection system that may visually locate a workpiece defect relative to the workpiece surface.

SUMMARY OF THE DISCLOSURE

According to a first aspect of the invention, a system is provided for inspecting a workpiece that includes a workpiece defect and a workpiece surface. The system includes a laser pointer connected to an ultrasonic inspection system. The ultrasonic inspection system includes an ultrasonic transducer that directs sound waves to the workpiece defect, where the sound waves contact the workpiece surface at a workpiece surface location. The laser pointer directs a laser beam against the workpiece surface to visually annunciate the workpiece surface location.

According to a second aspect of the invention, another system is provided for inspecting a workpiece that includes a workpiece defect and a workpiece surface. The system includes a manipulator system, an ultrasonic inspection system and a laser pointer. The ultrasonic inspection system includes an ultrasonic transducer that is connected to the manipulator system, that directs sound waves into the workpiece, and that senses reflected sound waves to detect a workpiece defect, where the sound waves intersect the workpiece surface at a workpiece surface location. The laser pointer is connected to the ultrasonic transducer, and directs a laser beam against the workpiece surface to visually mark the workpiece surface location associated with and indicative of the workpiece defect.

The foregoing features and the operation of the invention will become more apparent in light of the following description and the accompanying drawings.

BRIEF DESCRIPTION OF THE DRAWINGS

FIG. 6 is a side-sectional illustration of a laser pointer and an ultrasonic transducer included in the system illustrated in FIG. 5;

FIG. 7 is a cross-sectional illustration of the laser pointer and the ultrasonic transducer included in the system illustrated in FIG. 5; and FIG. 8 is a partial illustration of the workpiece surface during operation of the system illustrated in FIG. 5.

DETAILED DESCRIPTION OF THE INVENTION

Figure 1:
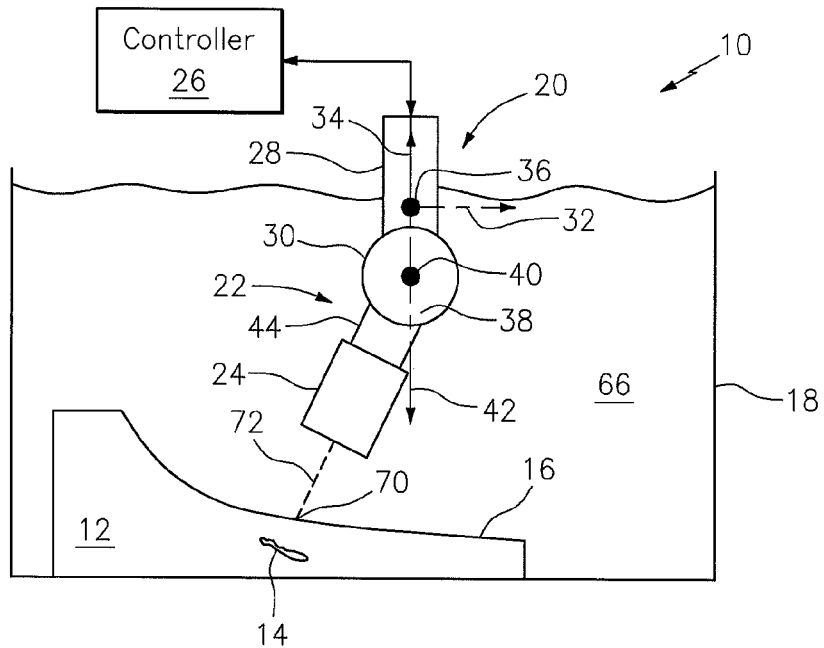
FIG. 1 is a side-sectional illustration of a workpiece inspection system during a first mode of operation.

FIG. 1 is a side-sectional illustration of a system 10 for inspecting (e.g., non-contact inspecting) a workpiece 12 that includes a workpiece defect 14 and a workpiece surface 16. The system 10 includes a liquid reservoir 18 (e.g., a water tank), a manipulator system 20, an ultrasonic inspection system 22, a laser pointer 24 and a controller 26.

The manipulator system 20 (e.g., a water-resistant, five-axis manipulator) may include one or more manipulators (e.g., multi-axis manipulators). The manipulator system 20 illustrated in FIG. 1, for example, includes a Cartesian robotic manipulator arm 28 and a polar robotic manipulator wrist 30. The manipulator arm 28 may translate along an x-axis 32, a y-axis 34 and/or a z-axis 36. The manipulator wrist 30 is connected to the manipulator aim 28, and includes a manipulator mounting segment 38 that may rotate about a first rotational axis 40 and/or a second rotational axis 42 (e.g., the y-axis 34).

Figure 2:
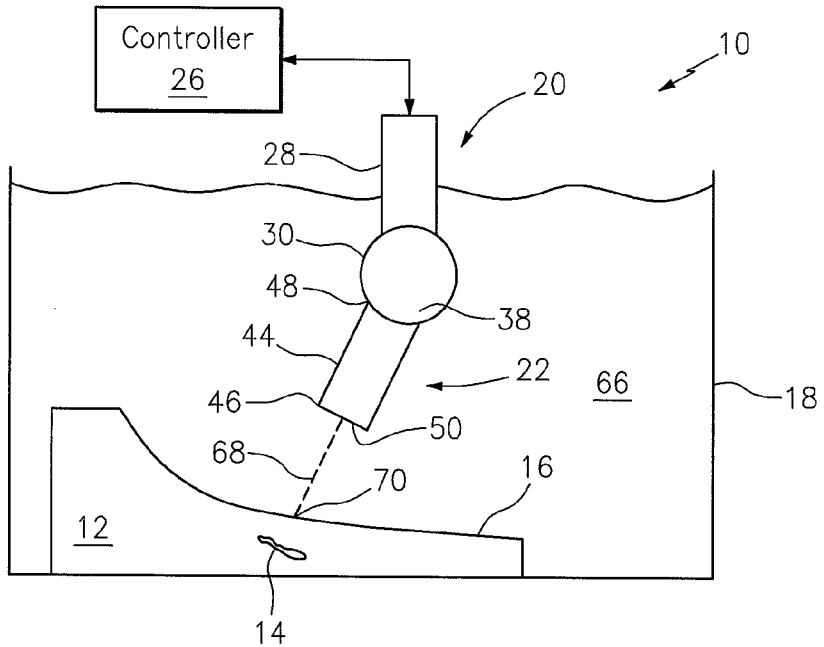
FIG. 2 is a side-sectional illustration of the workpiece inspection system during a second mode of operation.

The ultrasonic inspection system 22 includes an ultrasonic transducer 44. Referring to FIG. 2, the ultrasonic transducer 44 extends between a first transducer end 46 and a second transducer end 48, which is connected to the manipulator mounting segment 38. The ultrasonic transducer 44 includes an ultrasonic transducer surface 50 located at the first transducer end 46.

Figure 3:
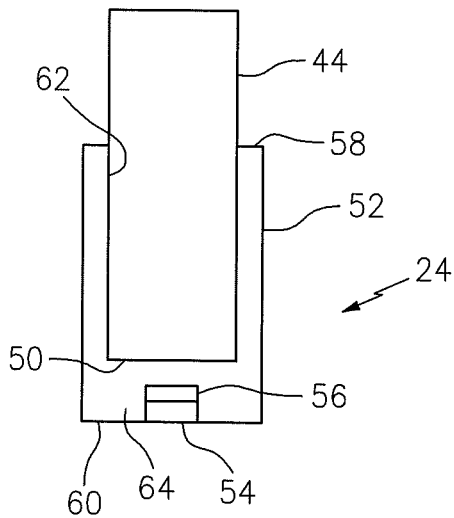
FIG. 3 is a side-sectional illustration of a laser pointer and an ultrasonic transducer included in the system illustrated in FIG. 1.

Referring to FIG. 3, the laser pointer 24 (e.g., a water-resistant laser pointer) includes a laser pointer housing 52, a laser 54 (e.g., a laser diode), and a power source 56 (e.g., a battery). The laser pointer housing 52 extends between a first housing end 58 and a second housing end 60. The laser pointer housing 52 may include a mounting bore 62 and a housing endwall 64. The mounting bore 62 extends axially through the laser pointer housing 52 from the first housing end 58 to the housing endwall 64. The laser 54 is located at the second housing end 60, and may be mounted in the housing endwall 64. The power source 56 may be connected to the laser 54 through, for example, a switch (not shown). The power source 56 may be mounted in the laser pointer housing 52, for example, in the housing endwall 64 between the laser 54 and the mounting bore 62. In alternative embodiments, the power source may be located external of the laser pointer housing 52.

Referring to FIG. 1, the controller 26 may be implemented using hardware, software, or a combination thereof. The controller may include, for example, one or more processors, a memory, analog and/or digital circuitry, etc. The controller 26 is in signal communication (e.g., hardwired or wirelessly connected) with the manipulator system 20 and the ultrasonic inspection system 22. In alternate embodiments, the manipulator system 20 and the ultrasonic inspection system 22 may each include a separate controller that may be networked together, or discretely operated.

Figure 4:
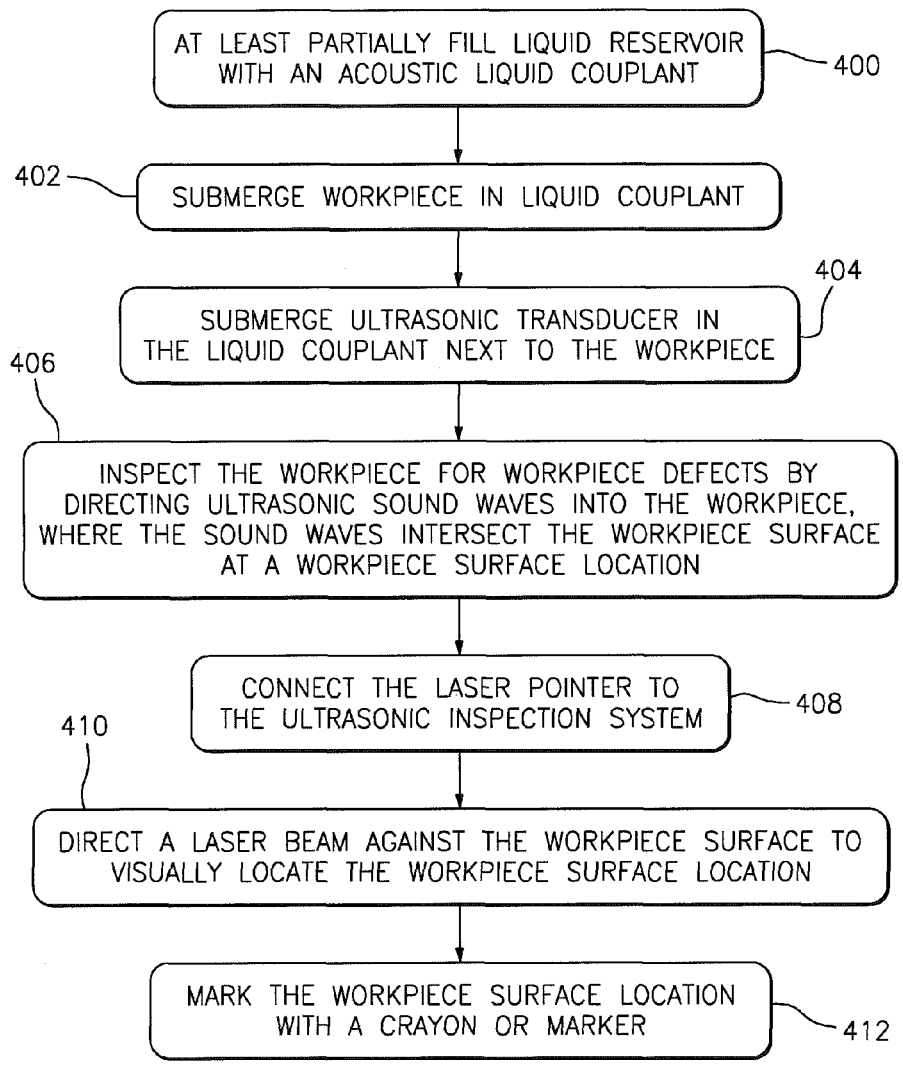
FIG. 4 is a flow diagram of a method for operating the system illustrated in FIGS. 1 and 2.

FIG. 4 is a flow diagram of a method for operating the system illustrated in FIGS. 1 and 2. Referring to FIGS. 2 and 4, in step 400, the liquid reservoir 18 is at least partially filled with an acoustic liquid couplant 66 (e.g., water). In step 402, the workpiece 12 (e.g., a component of a gas turbine engine) is positioned (e.g., submerged) in the liquid couplant 66. In step 404, the controller 26 signals the manipulator system 20 to move the ultrasonic transducer 44 into an inspection position where, for example, the ultrasonic transducer 44 is submerged in the liquid couplant 66 and is located next to the workpiece 12.

In step 406, the controller 26 signals the ultrasonic inspection system 22 to inspect the workpiece 12 for one or more workpiece defects 14 (e.g., voids, inclusions, cracks, or aberrant microstructure within the workpiece 12 material). The ultrasonic transducer 44, for example, directs ultrasonic sound waves from the ultrasonic transducer surface 50 through the liquid couplant 66 and into the workpiece 12 along a first trajectory 68. The sound waves contact (e.g., intersect) the workpiece surface 16 at a workpiece surface location 70. The ultrasonic transducer 44 may subsequently receive (e.g., detect) reflections of the sound waves through the ultrasonic transducer surface 50, and the ultrasonic inspection system 22 may provide a reflection signal indicative of the reflections to the controller 26. In a manual system, the controller 26 may process the reflection signal to determine whether a workpiece defect 14 is located within the workpiece 12 along the first trajectory 68. Where the workpiece defect 14 has not been detected, the steps 404 and 406 may be repeated for another (e.g., adjacent) inspection position. Where the workpiece defect 14 has been detected, however, the controller 26 may alert a system operator with, for example, a visual and/or audio indication. In an automated system, the reflection signals from a plurality of inspection positions about the workpiece may be plotted to an electronic map (c-scan) where the signals include, for example, background noise signals and/or defect signals. After the workpiece has been inspected and the map completed, the operator may move the transducer with the computer controlled axes to the inspection position(s) indicated in the c-scan map where defects occur.

Referring to FIGS. 1 and 4, in step 408, the laser pointer 24 is connected to the ultrasonic inspection system 22, for example, after the system operator is alerted through an alarm of a manual system or after review of the c-scan map in an automated system that the workpiece defect 14 was detected during the workpiece 12 inspection. Referring to FIG. 3, the mounting bore 62 may be placed over the ultrasonic transducer 44, for example, such that the ultrasonic transducer surface 50 contacts the housing endwall 64. The mounting bore 62 may be secured to the transducer 44, for example, through friction of a close tolerance fit that may utilize an item such as an O-ring. The mounting bore 62 may alternatively be secured to the transducer 44, for example, through a mechanical device such as a set-screw through the wall of the housing 52 that contacts the transducer case 44.

Referring again to FIGS. 1 and 4, in step 410, the laser 54 is switched on and directs a laser beam, along a second trajectory 72, against the workpiece surface 16. The second trajectory 72 may be substantially co-axial to the first trajectory 68 (see FIG. 2); i.e., the trajectory along which the workpiece defect 14 was detected. The laser beam therefore visually locates (e.g., marks with a point of light) the workpiece surface location 70 and, thus, a location on the workpiece surface 16 above the workpiece defect 14. In step 412, the workpiece surface location 70 may also be marked (e.g., indelibly marked) with, for example, a crayon or marker where the laser beam reflects against the workpiece surface 16.

In alternate embodiments, the laser may be mounted within the laser pointer housing adjacent to the ultrasonic transducer. In still other embodiments, the laser pointer may be connected to other ultrasonic inspection system components besides the ultrasonic transducer.

Figure 5:
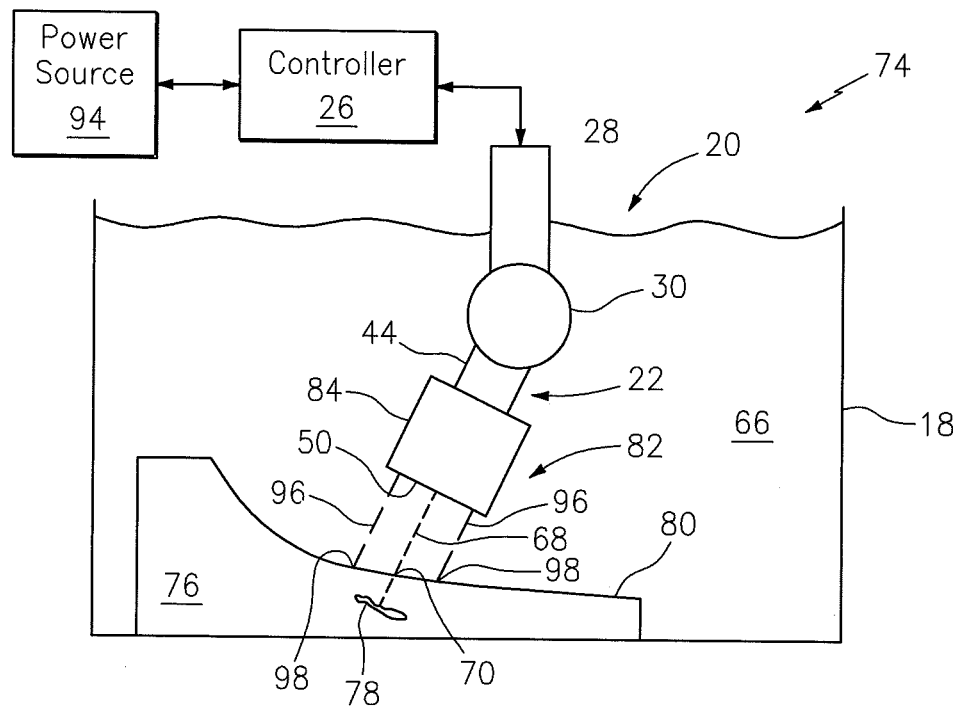
FIG. 5 is a side-sectional illustration of an alternate embodiment workpiece inspection system.

FIG. 5 is a side-sectional illustration of another system 74 for inspecting (e.g., non-contact inspecting) a workpiece 76 that includes a workpiece defect 78 and a workpiece surface 80. In contrast to the system 10 illustrated in FIG. 1, the system 74 in FIG. 5 includes an alternate embodiment laser pointer 82 (e.g., a water-resistant laser pointer).

FIG. 6 is a side-sectional illustration of the laser pointer 82 illustrated in FIG. 5. FIG. 7 is a cross-sectional illustration of the laser pointer 82 illustrated in FIG. 5. Referring to FIGS. 6 and 7, the laser pointer 82 includes a laser pointer housing 84 and a plurality of lasers 86 (e.g., laser diodes). The laser pointer housing 84 extends axially between a first housing end 88 and a second housing end 90, and includes a mounting bore 92. The mounting bore 92 extends axially through the laser pointer housing 84 between the first housing end 88 and the second housing end 90. The lasers 86 are arranged circumferentially around the mounting bore 92 at the second housing end 90. Referring to FIGS. 5 and 6, the lasers 86 may be connected to an external power source 94 through the controller 26. In alternative embodiments, a switch and an internal power source (e.g., one or more batteries) may be mounted in the laser pointer housing.

During operation of the system 74 illustrated in FIG. 5, the laser pointer 82 may be connected to the ultrasonic inspection system 22 before the ultrasonic inspection of the workpiece 76 (e.g., the step 406 in FIG. 4) because the laser pointer housing 84 does not obstruct the ultrasonic transducer surface 50. Referring to FIGS. 5 and 6, the controller 26 may signal each of the lasers 86 to direct a laser beam, along a respective second trajectory 96, against the workpiece surface 80, for example, after the workpiece defect 78 has been detected by the ultrasonic inspection system 22. Alternatively, the lasers 86 may direct the laser beams against the workpiece surface 80 during the ultrasonic inspection. The second trajectories 96 may be substantially parallel to the first trajectory 68 (i.e., the trajectory along which the workpiece defected was detected).

Referring to FIGS. 5 and 8, each laser beam visually marks the workpiece surface 80 with a respective point of light at a respective second workpiece surface location 98. The second workpiece surface locations 98 are located circumferentially around, and a distance 100 (e.g., a predetermined distance) from the workpiece surface location 70 (i.e., the point where the sound waves intersected the workpiece surface 80 along the first trajectory 68). A center between the second workpiece surface locations 98 therefore visually locates the workpiece surface location 70 and, thus, a location on the workpiece surface 80 above the workpiece defect 78.

In alternate embodiments, the lasers may be configured such that the laser beams converge together at a central point (e.g., the workpiece surface location).

While various embodiments of the present invention have been disclosed, it will be apparent to those of ordinary skill in the art that many more embodiments and implementations are possible within the scope of the invention. Accordingly, the present invention is not to be restricted except in light of the attached claims and their equivalents.

What is claimed is:

1. A system for inspecting a workpiece, comprising:
an ultrasonic inspection system comprising an ultrasonic transducer that directs sound waves to the workpiece, wherein the sound waves contact the workpiece surface at a first workpiece surface location; and
a laser pointer connected to the ultrasonic inspection system, wherein the laser pointer directs a laser beam against the workpiece surface to visually annunciate the first workpiece surface location;
wherein the laser beam is one of a plurality of laser beams directed from the laser pointer against the workpiece surface by the laser pointer, wherein each laser beam contacts the workpiece surface at a respective second workpiece surface location, and wherein the first workpiece surface location is centered between the second workpiece surface locations.

2. The system of claim 1, wherein the laser pointer comprises a water-resistant laser pointer.

3. The system of claim 1, wherein the laser pointer comprises a laser pointer housing mounted to the ultrasonic transducer.

4. The system of claim 3, wherein the laser pointer further comprises a plurality of lasers connected to the laser pointer housing, and arranged circumferentially around the ultrasonic transducer.

5. The system of claim 1, wherein the ultrasonic transducer is connected to a manipulator system.

6. The system of claim 5, wherein the manipulator comprises a robotic multi-axis manipulator system.

7. A system for non-contact inspecting a workpiece that includes a workpiece surface, comprising:
a manipulator system;
an ultrasonic inspection system comprising an ultrasonic transducer that is connected to the manipulator system, that directs sound waves into the workpiece, and that senses reflected sound waves to detect a workpiece defect, wherein the sound waves intersect the workpiece surface at a first workpiece surface location; and
a laser pointer connected to the ultrasonic transducer, wherein the laser pointer directs a laser beam against the workpiece surface to visually mark the first workpiece surface location associated with and indicative of the workpiece defect;
wherein the laser beam is one of a plurality of laser beams directed against the workpiece surface by the laser pointer, wherein each laser beam contacts the workpiece surface at a respective second workpiece surface location, and wherein the first workpiece surface location is located between the second workpiece surface locations.

8. The system of claim 7, wherein the laser pointer comprises a water-resistant laser pointer.

9. The system of claim 7, wherein the laser pointer comprises a plurality of lasers connected to a laser pointer housing, and arranged circumferentially around the ultrasonic transducer.

10. The system of claim 7, wherein the manipulator system comprises a robotic multi-axis manipulator.

* * * * *